United States Patent
Ishii et al.

(10) Patent No.: US 7,901,573 B2
(45) Date of Patent: Mar. 8, 2011

(54) SEPARATION COLUMN AND LIQUID CHROMATOGRAPHY APPARATUS USING THE SAME

(75) Inventors: Kimihiko Ishii, Hitachinaka (JP); Hironori Kaji, Hitachinaka (JP); Masahito Ito, Hitachinaka (JP); Yoshihiro Nagaoka, Ishioka (JP); Kunihiko Takao, Tsuchiura (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/081,572

(22) Filed: Apr. 17, 2008

(65) Prior Publication Data
US 2008/0283458 A1 Nov. 20, 2008

(30) Foreign Application Priority Data

Apr. 20, 2007 (JP) ................. 2007-111825
Mar. 19, 2008 (JP) ................. 2008-072072

(51) Int. Cl.
*B01D 15/08* (2006.01)
(52) U.S. Cl. ........................ 210/198.2; 210/656
(58) Field of Classification Search ........... 210/198.2, 210/656
See application file for complete search history.

(56) References Cited

U.S. PATENT DOCUMENTS

| | | | |
|---|---|---|---|
| 4,314,031 A | | 2/1982 | Sanford et al. |
| 4,968,421 A | * | 11/1990 | Spacek et al. ........... 210/198.2 |
| 2004/0236083 A1 | * | 11/2004 | Libert et al. ............. 210/656 |
| 2005/0155933 A1 | * | 7/2005 | Ma ............................ 210/656 |
| 2008/0099389 A1 | | 5/2008 | Nagaoka et al. |
| 2008/0202218 A1 | | 8/2008 | Nagaoka et al. |

FOREIGN PATENT DOCUMENTS

| | | | |
|---|---|---|---|
| DE | 19726164 A1 | * | 12/1998 |
| EP | 0 990 153 B1 | | 4/2000 |
| JP | 11-064314 | | 3/1999 |
| JP | 2002-505005 | | 2/2002 |
| JP | 2007-076756 | | 3/2007 |

OTHER PUBLICATIONS

Huang et al. "The mechanical performance and anti-corrosion behavior of diamond-like carbon film." Diamond and Related Materials. 12 (2003) 1406-1410.*
Wang et al. "Low temperature bonding for microfabrication of chemical analysis devices" Sensors and Actuators B. 45 (1997) 199-207.*
Liang et al. A graphitized-carbon monolithic column. Analytical Chemistry. vol. 75, No. 18 (2003) pp. 4901-4912.*

* cited by examiner

*Primary Examiner* — Krishnan S Menon
*Assistant Examiner* — Katherine Zalasky
(74) *Attorney, Agent, or Firm* — McDermott Will & Emery LLP

(57) ABSTRACT

Disclosed herein is a separation column comprising a porous block covered with a coating wherein space-free adhesion is attainable therebetween by low temperature process without releasing octadecylsilyl bases and others from the porous block. A monolith rod 1 is covered with a metal or resin coating 2. Then, the monolith rod 1 covered by the coating 2 is further covered with a rod retainer 3 made of a low melting point metal (melting point 100-200 degrees C.) to form a column body 19. Since the rod retainer 3 is formed by pressure molding at low temperature (100-200 degrees C.). It is therefore possible to absorb the surface irregularities of the monolith rod 1 by the coating 2 while octadecylsilyl bases and others from are released when the retainer 3 is formed. This allows the potential separation ability of the porous block to be brought out maximally.

16 Claims, 7 Drawing Sheets

SEPARATION COLUMN AND LIQUID CHROMATOGRAPHY APPARATUS USING THE SAME

BACKGROUND OF THE INVENTION

1. Field of the Invention

The present invention relates to a separation column which is used in high performance liquid chromatography or the like to separate components of samples and also to a liquid chromatography apparatus which uses it.

2. Description of the Related Art

In conventional high performance liquid chromatography or the like where a particulate-packed column is commonly used, increasing the amount of liquid delivered per unit time is needed to shorten the analysis time. However, to allow this while the same separation performance as before is provided, it is necessary to increase the surface area of the packed particulates by packing smaller particulates. Specifically, in the case of a conventional column which is a cylindrical container having an inside diameter of about 4 mm and filled with particulates of about 5 micrometers in diameter, it is possible to shorten the analysis time to a tenth if the particulates are made smaller to about 2 micrometers in diameter.

However, reducing the size of the particulates increases the flow resistance and therefore makes it necessary to enhance the whole analysis apparatus in pressure resistance since the liquid must be delivered at higher pressure.

As compared with the particulate-packed column, use of a monolith column, which is a skeleton like a three dimensional network having pores (channels, macropores and throughpores) integrated therein, provides a larger surface area. This column can have so large a porosity as not to increase the flow resistance. For example, such a column is a monolith type silica column formed by setting a porous block (monolith rod or monolithic silica rod) in a thin tube. Higher performance is aimed at by using this monolithic silica column.

However, since the porous block is difficult to form with precision in terms of outer diameter, bowing, etc., spaces are likely to occur between the thin tube and the porous block. Thus, as a first prior art technique, avoiding leakage of the mobile phase from the side surface of the column by coating the peripheral surface of the porous block with resin is disclosed in, for example, JP-A-1999-64314.

Also as a second prior art technique, it is known to heat a fiber-reinforced plastic tube in order to improve contact between the column frame and the monolithic absorbent after the monolithic molding is introduced into the tube.

SUMMARY OF THE INVENTION

However, the circumferential surface of the porous block has several micrometer to several ten micrometer irregularities. Therefore, the first prior art technique which coats the circumferential surface of the porous block with resin cannot secure ideal adhesion between the porous block and the resin coating, leaving narrow spaces. Further, since liquid is passed through the porous block at high pressure, the resin coating is likely to cause spaces due to the elasticity. As a matter of course, it is desirable not to cause these spaces since they remarkably deteriorate the separation performance as a column.

With the second prior art technique, the monolithic molding is heated to high temperature (for example, 500-600° C.). Therefore, in the case of a monolithic absorbent which comprises a silica gel substrate having octadecylsilyl bases bonded chemically therewith, it is possible that octadecylsilyl bases and others may be released, resulting in deterioration in the separation performance of the column. Since the effect of heating is especially large around the circumference of the monolithic molding, making the monolithic molding thinner in order to reduce the solvent flow rate may further deteriorate the separation performance of the column.

In addition, although the monolith rod used by the technique described in JP-A-1999-64314 is 4 mm or 4.6 mm in diameter not so different from the inner diameter around 5 mm of conventional particulate-packed columns, the mobile phase is more consumed due to the larger porosity of the monolithic rod. This consumption further increases if the liquid flow rate is raised in order to shorten the analysis time.

It is an object of the present invention to realize a separation column comprising a porous block covered with a coating wherein space-free adhesion is attainable at low temperature between the porous block and the coating without releasing octadecylsilyl bases and others from the porous block, and realizes a liquid chromatography apparatus which uses it so that the potential separation ability of the porous block is maximally brought out.

The present invention provides a monolith type separation column comprising a porous monolith rod whose circumferential surface is covered with a coating wherein a rod retainer is formed around the coating by pressure molding a low melting point inorganic material.

In addition, the above-mentioned separation column is used in liquid chromatography apparatus.

According to the present invention, it is possible to realize a separation column comprising a porous block covered with a coating wherein space-free adhesion is attainable between them without thermally releasing octadecylsilyl bases and others from the porous block, and a liquid chromatography apparatus which uses the separation column.

DETAILED DESCRIPTION OF THE PREFERRED EMBODIMENTS

Embodiments of the present invention will be described below with reference to the attached drawings.

Figure 1A:
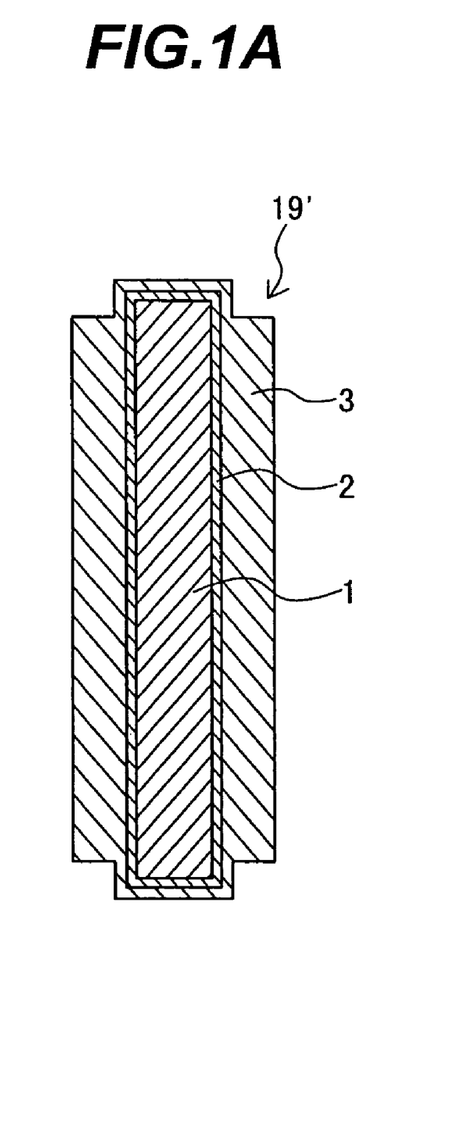
FIGS. 1A and 1B are an exemplary cross sectional views of a column body of a separation column, an embodiment of the present invention after a rod retainer is formed by pressure molding.
Figure 1B:
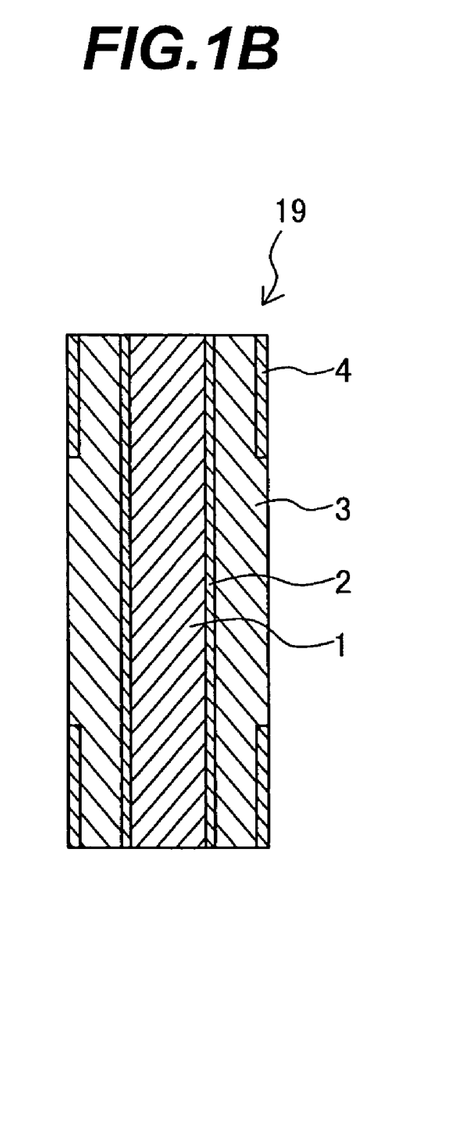

FIGS. 1A and 1B are exemplary cross sectional views of a column body 19 of a separation column, an embodiment of the present invention after a rod retainer is formed by pressure molding. In FIG. 1A, both ends of the column body 19 are not yet processed. The column body 19' in FIG. 1B is drawn after both ends are processed.

In FIG. 1A, a monolith rod (monolithic silica rod) 1 is a porous block which is shaped into a pillar and covered with a coating 2. Further, the coating 2 is covered with a rod retainer 3 by means of pressure molding. Employing a structure as shown in FIG. 1A makes it possible to tightly cover the monolith rod 1 with the coating 2 although the circumferential surface of the monolith thread 1 has several micrometer to several ten micrometer irregularities.

Since the monolith rod 1 is a sintered block, its strength is poor and external dimensions are not accurate. However, the rod retainer 3 supports the monolith rod 1 in strength, making it possible to strictly control the external dimensions of the column body 19.

The coating 2 is in contact with the outer surface of the monolith rod 1. To absorb irregularities of the outer surface, an elastic or thin material is suitable as the material of the coating 2. In addition, since a variety of solvents such as organic ones, acids and alkalis are to be passed through the monolith rod 1 in liquid chromatography, the material of the coating 2 must be highly anticorrosive.

Materials suitable for the coating 2 are highly anticorrosive metals such as gold, platinum and stainless steel, metal nitrides such as TiN, CrN, ZrN, and TiAlN, non-metallic materials such as DLC (Diamond like carbon), fluorocarbon resins such as PETF and FEP, polyimide resins such as Vesp and polyaryleneetherketone resins such as PEEK.

These materials can be formed as the coating 2 by various methods such as vapor deposition, sputtering, plating such as ion plating, heat-shrinkable tubing, painting of a drying/hardening liquid material and thin film binding(wrapping). Especially, the coating 2 is highly immune to compression and deformation due to great hardness if the material is selected from the above mentioned metals and DCL (Diamond like carbon). Specifically, vapor deposition is applicable to gold and platinum. Sputtering and ion plating are applicable to highly anticorrosive metals, metal nitrides and non-metal materials. Heat-shrinkable tubing is applicable to fluorocarbon resins. Hardening by drying or sintering is applicable to polyaryleneetherketone resins. Binding is applicable to highly anticorrosive metals, fluorocarbon resins, polyaryleneetherketone resins and polyimide resins.

The thickness of the coating 2 is 1-100 μm if a metal or non-metal material is used. In the case of a resin, the thickness is 0.5-1.0 mm.

Desirably, the material of the rod retainer 3 is selected so that the rod retainer 3 can easily be machined at ordinary temperature and can support the monolith rod 1 in strength in the ordinary operating temperature range of the separation column up to 95 degrees C. Specifically, the rod retainer 3 is required to be solid and hard at temperatures up to about 100 degrees C.

To form the rod retainer 3 by pressure molding, the material is required to have fluidity at high temperatures beyond 100 degrees C. However, if the temperature exceeds 200-300 degrees C., octadecylsilyl bases and others may be released, causing deterioration in the separation performance of the column. Thus, the material must be selected from those which begin to melt at temperatures between 100 and 200 degrees C.

The selectable materials whose melting points are in the range of 100 to 200 degrees include low melting point alloys and antifriction alloys which contain such metals as zinc, lead, tin, copper, bismuth, cadmium and antimony. By using such an alloy, it is possible to freely shape the rod retainer 3 in a hot chamber die-cast machine which can control the molding pressure while the liquid temperature is kept constant.

In addition, when the rod retainer 3 is formed by pressure molding, force acts to press the coating 2 against the monolith rod 1. This can eliminate spaces between the coating 2 and the circumferential surface of the monolith rod 1 having several micrometer to several ten micrometer irregularities.

The pressure to mold the rod retainer 3 is controlled so as not to exceed the fracture strength of the monolith rod 1. Desirably, the pressure is controlled not to exceed, for example, 20 MPa.

The material of the rod retainer 3 may be such a low melting point glass as described in U.S. Pat. No. 4,314,031 which begins to melt at a temperature between 100 and 200 degrees C. Such a low melting point glass which has superior chemical durability and moldability can be synthesized by use of acid-base reaction or sol-gel process.

To form the rod retainer 3 from a low melting point glass, the pressure molding method can be used. The following describes the procedure in detail. A mold having a cylindrical bottom formed therein is prepared. Inside this mold, the monolith rod 1 provided with the coating 2 is set. Jellified low melting point glass is put in the cavity between the internal wall of the mold and the outer surface of the coating 2. Then, pressurization is done from the top of the mold so that the cavity is filled with the low melting point glass and the coating 2 is deformed to attain tight contact with the monolith rod 1. Then, after cooling is done, the monolith rod 1 having a rod retainer 3 fixed around the outer surface thereof is released from the mold. This pressure molding may also be implemented by use of the above-mentioned die-cast machine. In this case, the extrusion pressure and time are set lower and longer respectively than when an alloy is used as the material of the rod retainer 3. This is because the fluidity of the softened low melting point glass is lower than that of the melted alloy. For example, whereas the extrusion pressure is set to 20 MPa for the alloy, the low melting point glass is given an extrusion pressure of about 10 MPa. The softened low melting point glass is slowly introduced into the mold.

Although the metal, non-metal or resin coating 2 is thin, the coating 2 can be kept in tight contact with the monolith rod 1 without being deformed since the coating 2 is surrounded by the rod retainer 3 (rigid body). Thus, the separation performance does not deteriorate even if a liquid is passed through the monolith rod 1 at high pressure. In addition, precision machining can be done easily after the pressure molding process since the column body 19 is a rigid body.

That is, as shown in FIG. 1B, both ends of the column body 19 shown in FIG. 1A are cut planar and, after a screw section 4 is formed, polished. This machining can be done precisely and easily since the column body 19 is a rigid body.

Figure 2A:
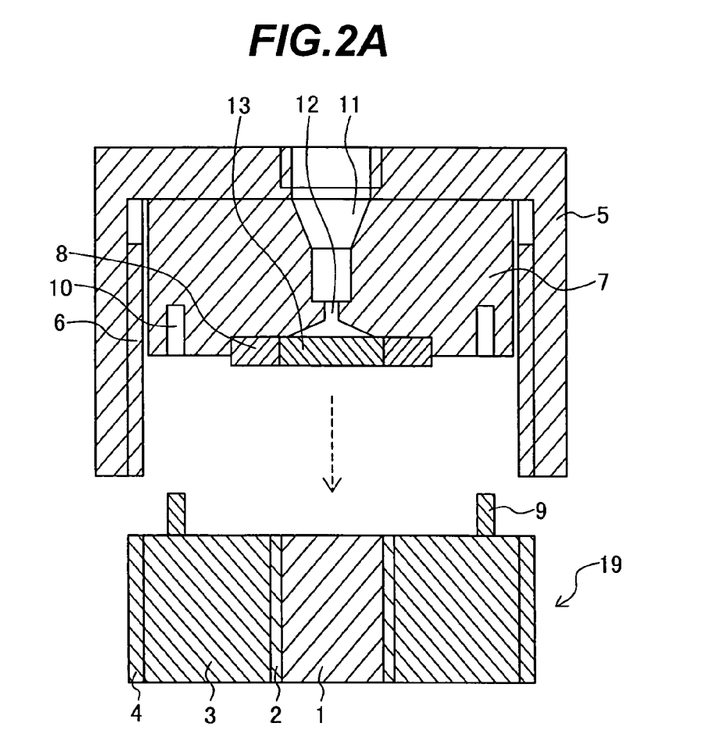
FIGS. 2A and 2B are views for assistance of explaining how the column body shown in FIG. 1 is set into the sample inflow section of the separation column.
Figure 2B:
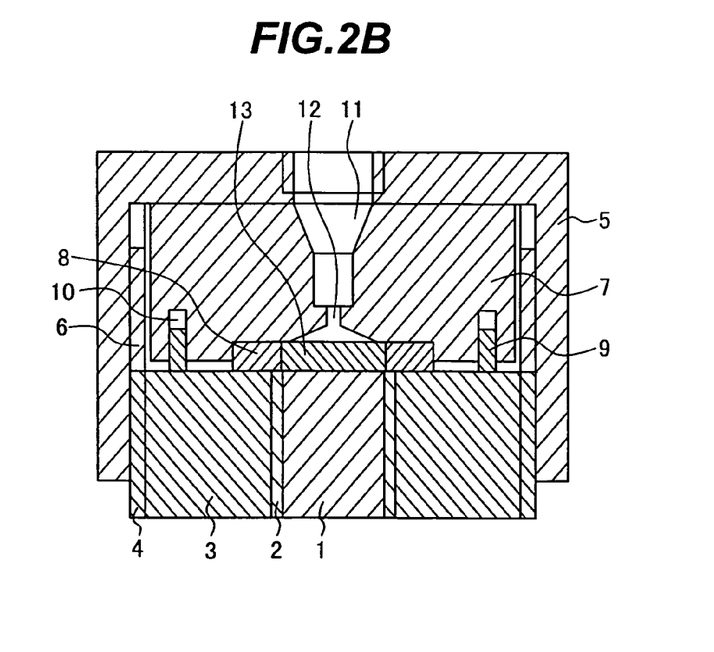

FIGS. 2A and 2B are views for assistance of explaining how the column body 19 shown in FIG. 1B is set into the sample inflow section of the separation column 1. FIG. 2A is a cross sectional view thereof before the setting is done. FIG. 2B is depicted after the setting is done.

Note that since the upper part of the separation column is identical with the lower part, that is, the inflow and outflow sides has the same structure, FIG. 2 depicts only the inflow half and omits the outflow side.

In FIG. 2A, the screw section 4 of the column body 19 is not yet engaged with the screw section 6 of a fixing member 5. In FIG. 2B, the screw sections 4 and 6 are mutually engaged. As described earlier, the column body 19 includes a monolith rod 1, a coating 2 and a rod retainer 3.

The fixing member 5 is rotated with respect to the rod retainer 3 so that the screw sections 4 and 6 are mutually engaged. A connecting member 7 is provided with a gasket 8. Rotating the fixing member 5 presses the gasket 8 against the end of the column body. Bosses 9 provided on the end of the rod retainer 3 are located in pits 10 provided in the connecting member 7. Therefore, rotating the fixing member 5 does not rotate the gasket 8 pressed against the end of the column body 19 since the connecting member 7 does not rotate.

Thus, since sealing is secured between the connecting member 7 and the gasket 8 and between the gasket 8 and the coating 2, high pressure liquid flowing into the monolith rod 1 does not leak outward from the separation column 1.

An inflow pipe (not shown in the figure) is connected to the junction section 11 of the connecting member 7. The sample to be separated and the mobile phase enter the separation column from the inflow port 12. The inflowing sample and mobile phase are radially diffused when they pass a diffusion member 13 before entering the monolith rod 1. While the sample moves toward the outflow side (downward in the figure), absorption and desorption are repeated. Consequently, the sample is separated into constituent chemical components for detection by a detector (not shown in the figure) disposed downstream of the outlet of the separation column.

The diffusion member 13 is constituted inside the gasket 8. The diffusion member 13 diffuses and introduces the sample into the monolith rod 1. The outside diameter of the diffusion 13 or the inside diameter of the gasket 8 is equal to or a little smaller than the outside diameter of the monolith rod 1. More specifically, if the diameter is smaller than the outside diameter of the monolith rod 1 and larger than 80% of the outside diameter, the liquid flowing into the column does not touch the rod retainer 3 at the upper end. This is desirable since the rod retainer 3 is inferior in corrosion resistance to the coating 2 and therefore elution of impurities other than the components of the sample is suppressed.

To realize a liquid chromatography apparatus capable of raising the pressure of the mobile phase entering the separation column (up to 5-30 MPa) in order to shorten the analysis time, the diameter of the monolith rod 1 is designed to be 1.2-2.8 mm and desirably 1.2-2 mm. The length of the separation column 1 in the flow direction is 30 mm-200 mm depending on the sample to be separated. It is therefore desirable to prepare monolith rods 1 which respectively measure 2 mm and 2.3 mm in diameter and 30, 50, 75, 100, 125 and 150 mm in length.

If liquid is delivered at the same pressure into a monolith rod 1 having a certain ratio of the porous cross section area or porosity, the amount of liquid delivered or the consumption of mobile phase per unit time is inversely proportional to the cross section area of the monolith rod 1. Thus, as compared with a conventional monolith rod having a diameter of about 4 mm, a monolith rod of the present invention with a diameter of about 2 mm can reduce the consumption of mobile phase to a fourth.

In view of practicability, it is possible to provide a convenient column which allow flow rates of 1.0 ml/min or lower employed commonly in general purpose high performance chromatography apparatus.

As described so far, it is possible to manufacture a separation column comprising a monolithic silica rod member covered with a highly anticorrosive coating wherein even under high pressure, space-free adhesion is secured between the rod and the coating since the separation column process temperature is not so high as to release octadecylsilyl bases and others. Using this monolithic silica rod member allows a liquid chromatography apparatus to implement high separation performance with less consumption of the mobile phase.

Figure 3A:
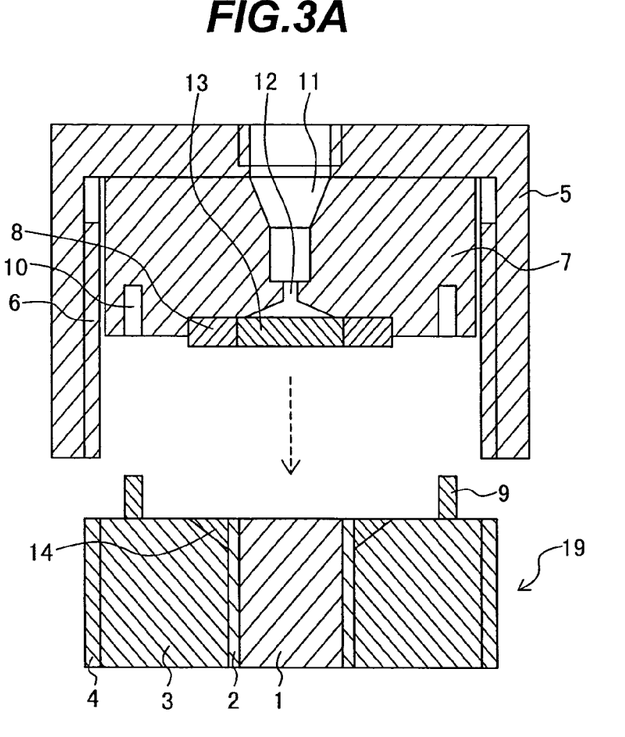
FIGS. 3A and 3B are views showing another separation column embodiment of the present invention in order to explain the column body is set into the sample inflow section.
Figure 3B:
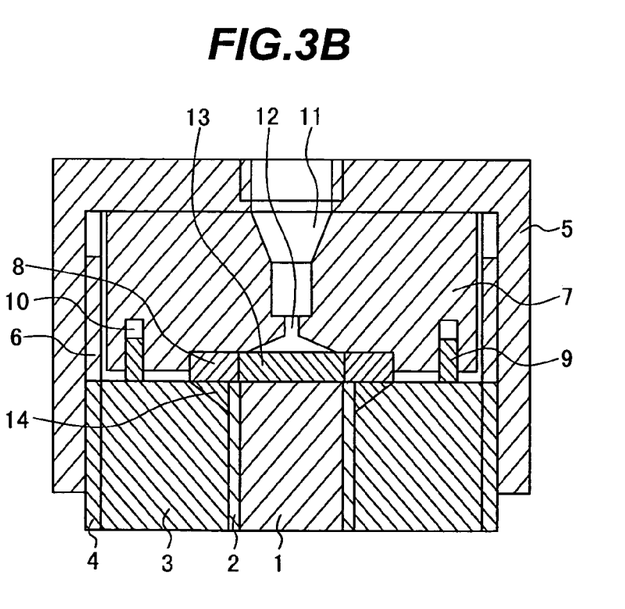

The upper end of the monolith rod 1 may be shaped as shown in FIGS. 3A and 3B. Specifically, when both ends of the column body 19 shown in FIG. 1A are processed, the upper end of the rod retainer 3 is dented around its inner circumference. This dent 14 is filled with the material of the coating 2 or a material substantially equivalent in corrosion resistance to the material of the coating 2. Alternatively, a highly elastic resin or rubber block which is cut or shaped somewhat larger than the dent 14 is set therein (not shown in the figure) so that it is pressed/deformed by the gasket 8 to secure tight contact. Consequently, the upper part of the coating 2 is extended on the upper end of the cylindrical monolith rod 1 in the radial direction thereof.

Owing to the configuration as shown in FIGS. 3A and 3B, even if the coating 2 is extremely thin, the area of contact with the gasket 8 is secured to enhance the liquid tightness since the dent 14 is filled with a highly anticorrosive material. That is, elution of impurities can be suppressed since it is possible to further prevent the mobile phase from touching the rod retainer 3.

Figure 4A:
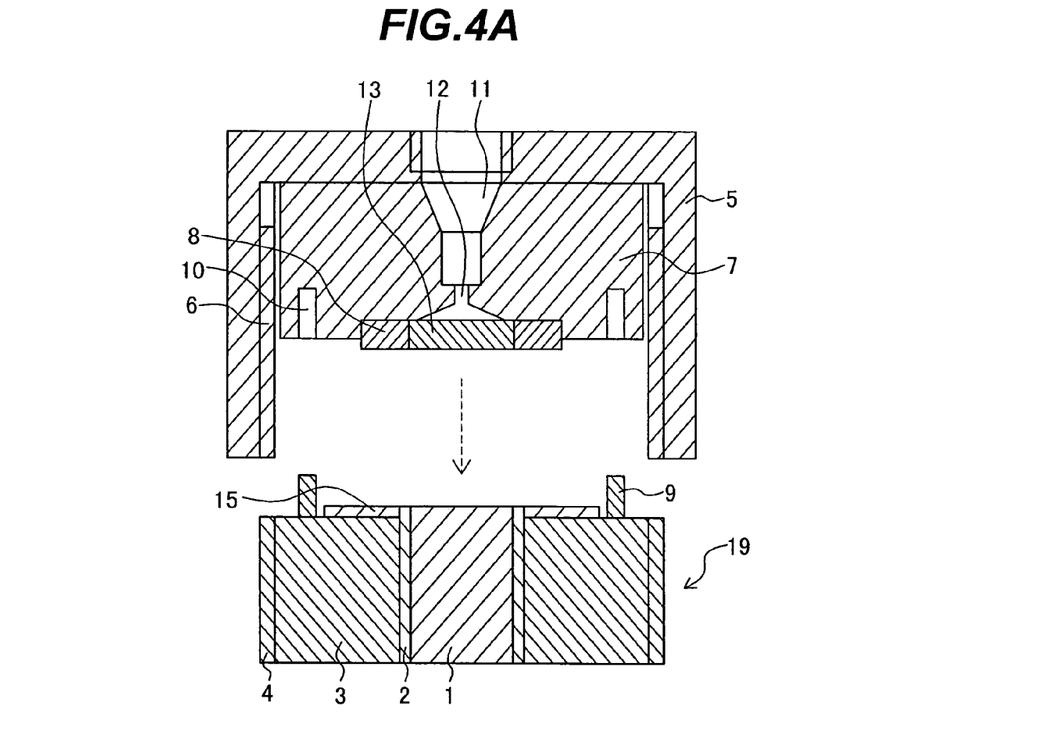
FIGS. 4A and 4B are views showing still another separation column embodiment of the present invention in order to explain the column body is set into the sample inflow section.
Figure 4B:
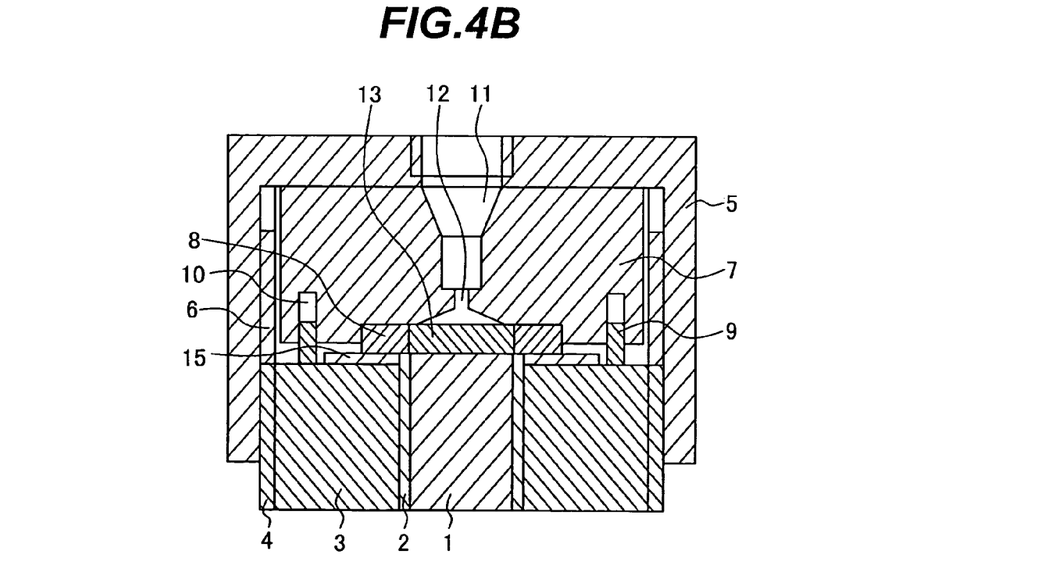

It is also possible to shape the upper end of the monolith rod 1 as shown in FIGS. 4A and 4B. Specifically, when both ends of the column body 19 shown in FIG. 1A are processed, the monolith rod 1 and the coating 2 are made somewhat longer than the rod retainer 3 and a coating 15 is formed around them. The material of the coating 15 is that of the coating 2 or a material which is substantially equivalent in corrosion resistance to the material of the coating 2. The coating 15 may be formed by inserting a doughnut-shaped member. This method is appropriate if the coating 2 is made of such a material as a metal, metal nitride, fluorocarbon resin or polyimide resin. The coating 15 may also be formed on the end of the column body 19 by masking the end of the monolith rod 1, performing vapor deposition, sputtering or ion plating and removing the mask. Vapor deposition, sputtering and ion plating are appropriate if the coating 2 is made of such a material as a metal or metal nitride. Ion plating is appropriate if the coating 2 is made of DLC.

Due to the configuration as shown in FIGS. 4A and 4B, even if the coating 2 is extremely thin, the area of contact with the gasket 8 is secured to enhance the liquid tightness. That is, elution of impurities can be suppressed since it is possible to further prevent the mobile phase from touching the rod retainer 3.

Figure 5A:
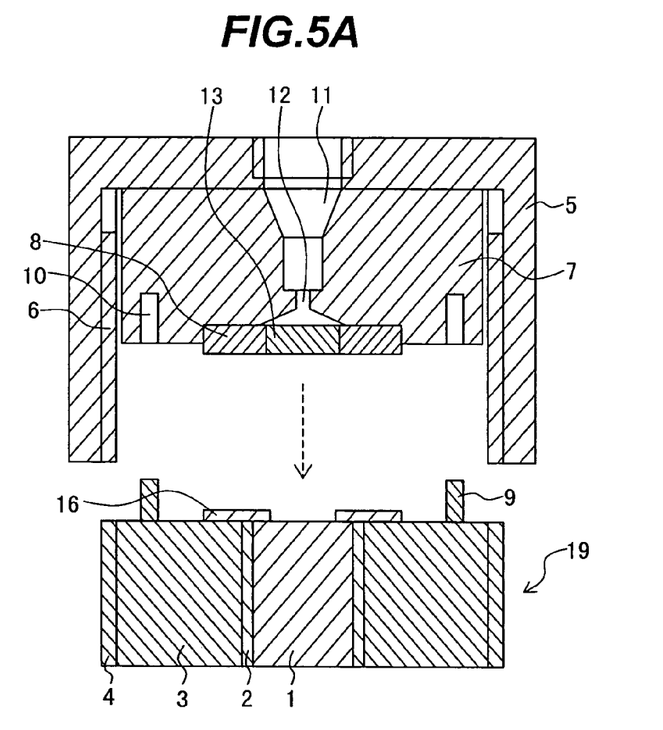
FIGS. 5A and 5B are views showing still another separation column embodiment of the present invention in order to explain the column body is set into the sample inflow section.
Figure 5B:
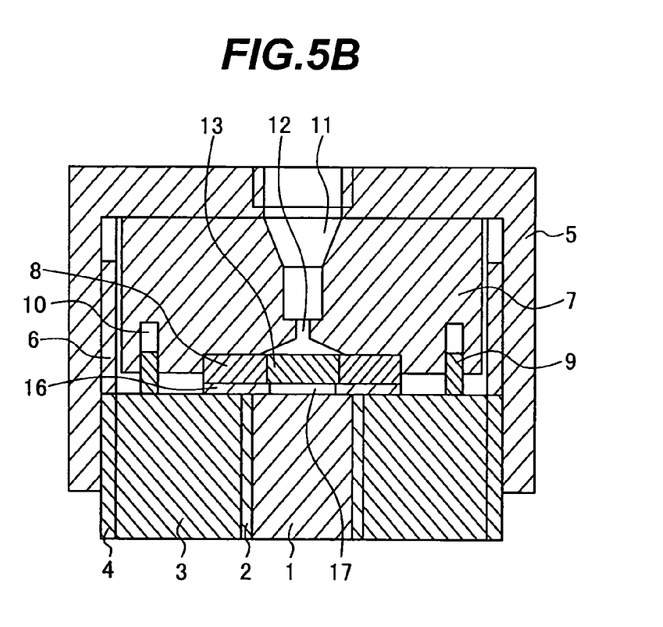

It is also possible to shape the upper end of the monolith rod 1 as shown in FIGS. 5A and 5B. Specifically, after both ends of the column body shown in FIG. 1A are processed, a coating 16 is formed on the end surface. The material of the coating 16 is that of the coating 2 or a material which is substantially equivalent in corrosion resistance to the material of the coating 2. The coating 16 is formed by inserting a doughnut-shaped member. Alternatively, the coating 16 may be formed on the end of the column body 19 by masking the end of the monolith rod 1, performing vapor deposition, sputtering or ion plating and removing the mask.

The outer diameter of the diffusion member 13 or the inner diameter of the gasket 8 is somewhat smaller than the outer diameter of the monolith rod 1. More specifically, the inner diameter of the gasket 8 is about 80% of the outer diameter of the monolith rod 1. The space 17 formed between the diffusion member 13 and the upper surface of the monolith rod 1 can be reduced to a substantially negligible volume by making the coating 16 extremely thin or employing a highly elastic material.

Due to the configuration as shown in FIGS. 5A and 5B, even if the coating 2 is extremely thin, it is relatively easy and inexpensive to enhance the liquid tightness between the gasket 8 and the monolith rod 1. That is, elution of impurities does not occur since it is possible to further prevent the mobile phase from touching the rod retainer 3.

Figure 6A:
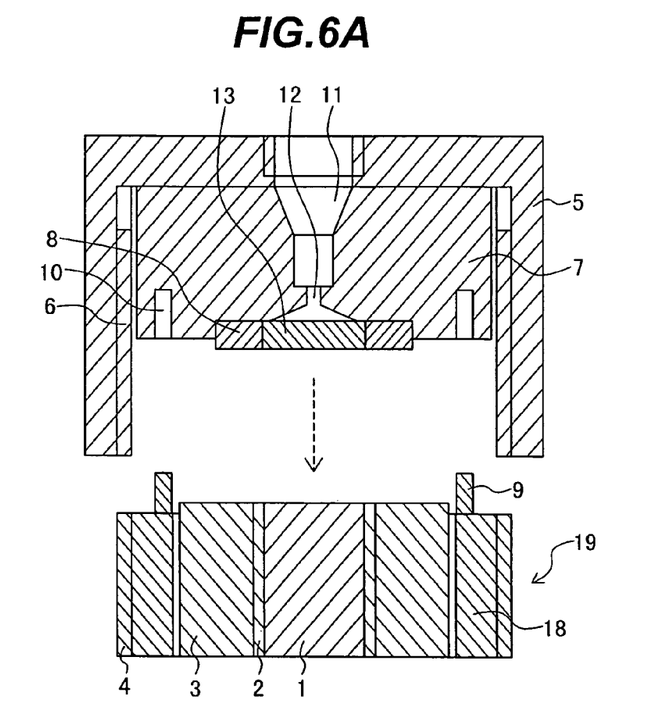
FIGS. 6A and 6B are views showing still another separation column embodiment of the present invention in order to explain the column body is set into the sample inflow section.
Figure 6B:
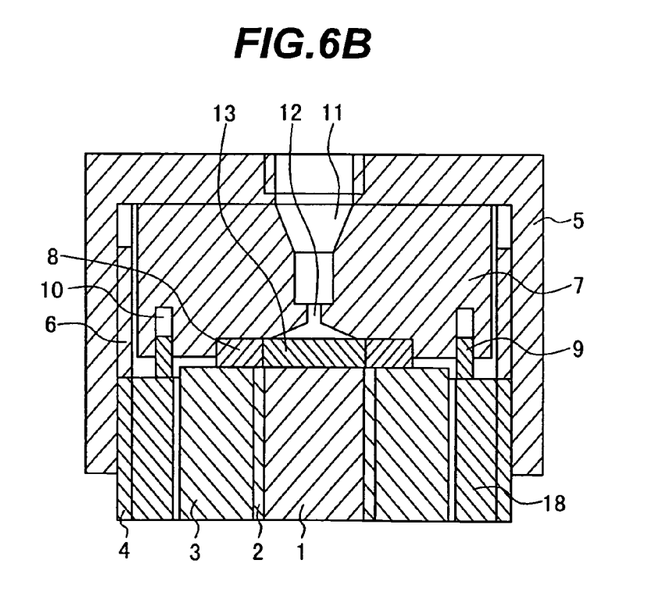

Further, an outer holder 18 may be arranged around the column body 19 as shown in FIGS. 6A and 6B. In this case, the screw section 4 and the bosses 9 are formed on the outer holder 18 and the outer diameter of the column body 19 is smaller than those shown in FIG. 1 through FIGS. 5A and 5B.

The fixing member 5 is rotated with respect to the outer holder 18 so that the screw sections 4 and 6 are mutually engaged. A connecting member 7 is provided with a gasket 8. Rotating the fixing member 5 presses the gasket 8 against the upper end of the column body 19. The bosses 9 provided on the end of the outer holder 18 are located in pits 10 provided in the connecting member 7. Therefore, rotating the fixing member 5 does not rotate the gasket 8 pressed against the end of the column body since the connecting member 7 does not rotate. Thus, since sealing is secured between the connecting member 7 and the gasket 8 and between the gasket 8 and the coating 2, high pressure liquid flowing into the monolith rod 1 does not leak outward from the separation column 1.

The configuration shown in FIGS. 6A and 6B allows the material of the outer holder 18 to be selected from a wider range of materials including highly anticorrosive ones and highly stiff ones. More specifically, the outer holder 18 is made of a stainless steel or PEEK (polyetheretherketone). This secures the strength of the screw section 4, eliminating the leakage from the junction section 11 of the connecting member 7 which would otherwise corrode the outside of the separation column.

As described so far, according to the present invention, a column body 19 is formed by covering a monolith rod 1 with a coating 2 (metal, non-metal or resin) and further with a rod retainer 3 made of a low melting point metal or glass (melting point 100-200 degrees C.). Since the rod retainer 3 is formed by pressure molding at low temperature (100-200 degrees C.), octadecylsilyl bases and others are not released from the monolith rod 1. It is therefore possible to realize space-free adhesion between the porous block and the coating, allowing the potential separation ability of the porous block to be brought out maximally.

Figure 7:
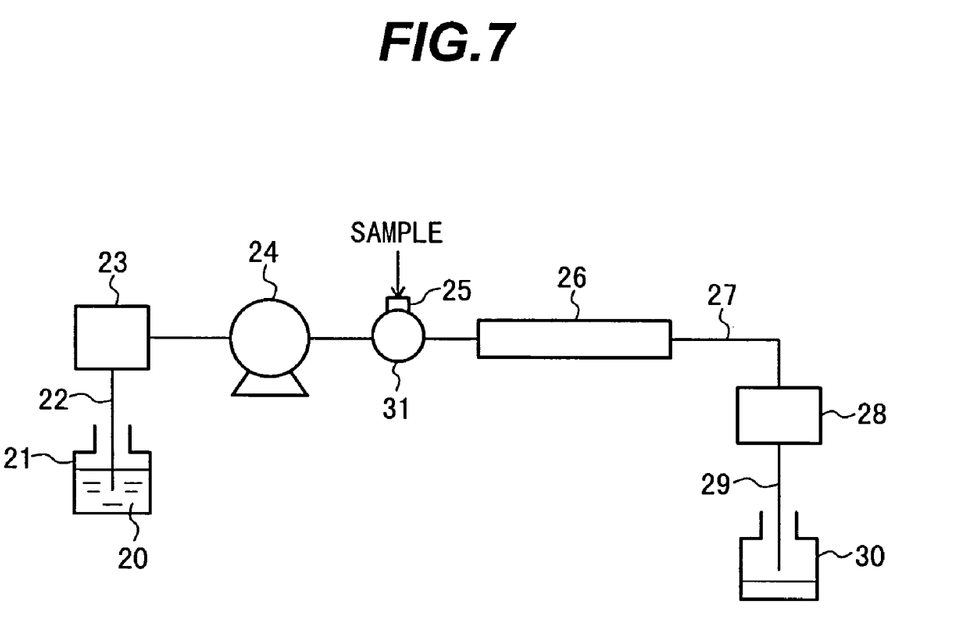
FIG. 7 is a view schematically showing the configuration of a liquid chromatography apparatus where an separation column of the present invention is applied.

FIG. 7 schematically shows the configuration of a liquid chromatography apparatus where the above-mentioned separation column of the present invention is applied.

In FIG. 7, the liquid chromatography apparatus includes an eluent storage reservoir 21, a deaeration device 23, a liquid delivery pump (liquid delivery unit) 24, an injector (liquid sample supply unit) 31, a separation column 26, a detector 28 and a waste liquid reservoir 30. Eluent 20 is drawn from the eluent storage reservoir 21 via the liquid delivery pump 24 and the pipe 22. The drawn eluent 20 is deaerated by the deaeration device 23 before the liquid delivery pump 24.

The eluent delivered from the liquid delivery pump 24 is supplied to the injector 31. The sample under componential analysis is injected from the injection port 25 thereof. The sample injected from the injection port 25 is mixed with the eluent 20 and sent to the separation column 26. The sample is separated into components of analytical interest and sent to the detector 28 via the pipe 27.

The detector 28 includes a light source, flow cell, optical sensor and others not shown in the figure. Components contained in the sample are detected by the detector 28. After detection processing is complete in the detector 28, the sample is sent to the waste liquid collection reservoir 30 via the pipe 29.

If the above-mentioned column body 19 is used in the separation column 26 of the liquid chromatography apparatus, it is possible to shorten the analysis time by raising the liquid flow rate without increase in the consumption of solvent.

Modes for carrying out the present invention may include that (A) the coating is made of a resin; (B) the outer holder is disposed around the circumferential surface of the rod retainer; (C) the coating is made of a polyaryleneetherketone resin, fluorocarbon resin or polyimide resin; (D) the outer holder is made of a metal; (E) the outer holder is made of a resin; and (F) the metal coating is formed around the circumferential surface of the monolith rod by vapor-deposition, sputtering, ion-plating or other plating.

What is claimed is:

1. A separation column of a monolith type comprising:
a cylindrical monolith rod formed from a porous block to take in a sample and mobile phase;
a coating formed around the circumferential surface of the monolith rod; and
a rod retainer disposed around the outer surface of the coating;
wherein the rod retainer is formed by pressure molding an inorganic material having a melting point between 100° C. and 200° C., and
further comprising a denting portion formed at an end of the column body;
wherein:
the denting portion is filled with the material of the coating or a material substantially equivalent in corrosion resistance to the material of the coating,
the denting portion is configured not to be in direct contact with the mobile phase, and the rod retainer having a lower corrosion resistance compared with the coating does not contact the mobile phase, and
the denting portion is pressed by a gasket.

2. A separation column according to claim 1 wherein:
the inorganic material is a metal.

3. A separation column according to claim 2 wherein:
the metal is an alloy containing zinc, lead, tin, copper, bismuth, cadmium and antimony.

4. A separation column according to claim 1 wherein:
the inorganic material is a glass.

5. A separation column according to claim 4 wherein:
the softening point of the glass is between 100 and 200 degrees C.

6. A separation column according to claim 1 wherein:
the rod retainer is formed around the outer surface of the coating by pressure molding under a pressure of not more than 20 MPa while the temperature of the inorganic material is kept substantially constant.

7. A separation column according to claim 1 wherein:
the coating is a metal or non-metal coating.

8. A separation column according to claim 7 wherein:
the metal coating is made of such a metal as gold, platinum or stainless steel or such a metal nitride as TiN, CrN, ZrN or TiAlN, and the non-metal coating is made of DLC (Diamond like carbon).

9. A separation column according to claim 1 wherein:
the upper part of the coating is extended on the upper end of the cylindrical monolith rod in the radial direction thereof.

10. A separation column according to claim 1 wherein:
the monolith rod has a diameter of 1.2 to 2.8 mm and a length of 30 mm to 200 mm.

11. A liquid chromatography apparatus comprising:
liquid sample supply unit for supplying a sample;
a separation column for separating analytes from the sample supplied by the sample supply unit;

a liquid delivery unit for delivering an eluent into the separation column to extract analytes from the separation column; and a detection unit for detecting delivered components of analytical interest;

wherein the separation column comprises a cylindrical monolith rod formed from a porous block, a coating formed around the circumferential surface of the monolith rod, and a rod retainer formed around the outer surface of the coating by pressuring molding an inorganic material having a melting point between 100° C. and 200° C., further comprising a denting portion which is formed at an end of the column body, wherein:

the denting portion is filled with the material of the coating or a material substantially equivalent in corrosion resistance to the material of the coating, the denting portion is configured not to be in direct contact with the mobile phase, and the rod retainer having a lower corrosion resistance compared with the coating does not contact the mobile phase, and the denting portion is pressed by a gasket.

12. The separation column according to claim 1, further comprising a second coating formed around said monolith rod and said coating material.

13. A method of manufacturing the separation column of claim 1, comprising the steps:

arranging said monolith rod in a mold and forming said coating around said monolith rod, adding said low melting point inorganic rod retainer material in spaces between the mold and the coating, and pressure molding said monolith rod and said coating with said rod retainer.

14. The separation column according to claim 1, wherein a screw section is formed on both sides of said rod retainer.

15. The separation column according to claim 1, wherein said coating is applied directly around all outer surfaces of said monolith rod.

16. The separation column according to claim 15, wherein said coating has a thickness of between 1.0 μm to 1000 μm.

* * * * *